United States Patent
Yu et al.

(10) Patent No.: US 9,322,038 B2
(45) Date of Patent: Apr. 26, 2016

(54) SIMULTANEOUS SACCHARIFICATION AND FERMENTATION(SSF) OF LIGNOCELLULOSIC BIOMASS FOR SINGLE CELL OIL PRODUCTION BY OLEAGINOUS MICROORGANISMS

(75) Inventors: Xiaochen Yu, Pullman, WA (US); Jijiao Zeng, Pullman, WA (US); Yubin Zheng, Pullman, WA (US); Mahesh Bule, Pullman, WA (US); Shulin Chen, Pullman, WA (US)

(73) Assignee: Washington State University, Pullman, WA (US)

( * ) Notice: Subject to any disclaimer, the term of this patent is extended or adjusted under 35 U.S.C. 154(b) by 52 days.

(21) Appl. No.: 14/130,986

(22) PCT Filed: Jul. 6, 2012

(86) PCT No.: PCT/US2012/045668
§ 371 (c)(1),
(2), (4) Date: May 5, 2014

(87) PCT Pub. No.: WO2013/006755
PCT Pub. Date: Jan. 10, 2013

(65) Prior Publication Data
US 2014/0234919 A1    Aug. 21, 2014

Related U.S. Application Data

(60) Provisional application No. 61/504,798, filed on Jul. 6, 2011.

(51) Int. Cl.
*C12P 19/02* (2006.01)
*C12P 19/14* (2006.01)
*C12P 7/64* (2006.01)
*D21C 1/08* (2006.01)

(52) U.S. Cl.
CPC .............. *C12P 7/6409* (2013.01); *C12P 7/6463* (2013.01); *C12P 2203/00* (2013.01); *Y02E 50/343* (2013.01)

(58) Field of Classification Search
USPC ......................................... 435/134

IPC ............... C12P 19/02,19/14, 2201/00, 2203/00, C12P 7/6409, 7/6463, 7/64; D21C 1/08; Y02E 50/343
See application file for complete search history.

(56) References Cited

U.S. PATENT DOCUMENTS

| | | | |
|---|---|---|---|
| 4,237,226 A * | 12/1980 | Grethlein | 435/99 |
| 8,802,409 B2 * | 8/2014 | Yu et al. | 435/171 |
| 2009/0217569 A1 * | 9/2009 | Pastinen et al. | 44/308 |
| 2010/0330615 A1 | 12/2010 | Neto | |

FOREIGN PATENT DOCUMENTS

| WO | 2010/046051 A2 | 4/2010 |
|---|---|---|
| WO | 2011/073781 A2 | 6/2011 |

OTHER PUBLICATIONS

1961 Beta-glucosidase1961—IUB, UBMB. http://www.chem.qmul.ac.uk/iubmb/enzyme/EC3/2/1/37.html . printed Aug. 10, 2015.B definition.*
1961 Cellulase—IUBMB definition, UBMB. http://www.chem.qmul.ac.uk/iubmb/enzyme/EC3/2/1/37.html . printed Aug. 10, 2015.*
1965 Beta-Xylosidase-IUBMB. http://www.chem.qmul.ac.uk/iubmb/enzyme/EC3/2/1/37.html . printed Aug. 15, 2015.*
Economou et al. 2010. Semi-solid state fermentation of sweet sorghum for the biotechnological production of single cell oil. Bioresource Technology, vol. 101, pp. 1385-1388.*
Gnansounou et al. 2005. Refining sweet sorghum to ethanol and sugar: economic trade-offs in the context of North China. Bioresource technology, vol. 96, pp. 985-1002.*
Yu et al., "Oil production by oleaginous yeasts using the hydrolysate from pretreatment of wheat straw with dilue sulfuric acid". Biosour Technol., Apr. 3, 2011, vol. 102(10), pp. 6134-6140.

* cited by examiner

*Primary Examiner* — Debbie K Ware
*Assistant Examiner* — Kailash C Srivastava
(74) *Attorney, Agent, or Firm* — Whitham Curtis Christofferson & Cook, PC

(57) ABSTRACT

Methods for producing lipids from lignocellulosic biomass are provided. Sugars produced by pretreatment of lignocellulosic biomass are utilized by heterotrophic oleaginous fungi or yeast to increase their biomass and to produce lipids without prior detoxification of the pretreated biomass. After the fungi/yeast are cultured with the sugars, solid residues from the pretreated biomass are combined with the fungi/yeast under conditions which allow simultaneous 1) enzymatic degradation of cellulose and/or hemicellulose to produce sugars and 2) fermentation of the sugars for further increases in biomass and lipid production.

13 Claims, 9 Drawing Sheets

SIMULTANEOUS SACCHARIFICATION AND FERMENTATION(SSF) OF LIGNOCELLULOSIC BIOMASS FOR SINGLE CELL OIL PRODUCTION BY OLEAGINOUS MICROORGANISMS

BACKGROUND OF THE INVENTION

1. Field of the Invention

The invention relates to methods and systems for lipid production by oleaginous fungi and yeasts. In particular, sugars produced by pretreatment of biomass are separated from solid residues and used by oleaginous fungi or yeast to produce biomass and lipids, while solid residue is subjected to Simultaneous Saccharification (by cellulase and/or hemicellulase enzymes) and Fermentation (by oleaginous fungi or yeast) to also produce biomass and lipids.

2. Background of the Invention

The vast amount of lignocellulosic biomass such as crop straw remains underutilized in spite of great progress from decades of biofuel research and development efforts. At the same time, it is a daunting challenge for the nation to meet the 36 billion gallons per year biofuel production target by 2022 as mandated by the Renewable Fuel Standard. Producing "drop-in" biofuel has attracted great interest; however, various conversion routes suffer from lack of practical near-term options. Both significant improvement to existing technology and novel strategies for developing new technical options are needed to make significant advancements. Lignocellulosic biomass which contains mainly cellulose, hemicelluloses and lignin are considered as ideal renewable carbon source and can be converted to fermentable sugars upon pretreatment and enzymatic hydrolysis for culture of heterotrophic oleaginous microbes, such as yeast and filamentous fungi, to produce lipid. An effective pretreatment technology results in the disruption of cell wall physical barriers as well as cellulose crystallinity and association with lignin to enhance the accessibility of hydrolytic enzymes to biomass macrostructure, thereby increasing the yield of final products. Numerous pretreatment methods have been evaluated. In particular, pretreatment by dilute acid, with pH control, by ammonia, and with lime appear among the most promising options (Chang et al., 1997; Chang et al., 1998; Dale et al., 1985; Heitz et al., 1991; Holtzapple et al., 1991; Iyer et al., 1996; Mackie et al., 1985; Ramos et al., 1992; Saddler et al., 1993; Weil et al., 1998; Weil et al., 1997; Wyman et al., 2005; Yoon et al., 1995). Generally pretreatment processes mainly remove either hemicelluloses (eg. dilute sulfuric acid, hot water) or lignin (eg. lime, ammonia fiber explosion) as dissolved sugars or lignin-derived products in the pretreatment hydrolysate. Previous publications (Huang et al., 2009; Yeshitila Asteraye Tsigie et al., 2012; Yu et al., 2011) reported that the hydrolysate from dilute sulfuric acid pretreatment of lignocellulosic biomass could be effectively utilized by oleaginous yeasts. On the other hand, the remaining pretreated solid residues could be enzymatically hydrolyzed into monomeric sugars for further fermentation.

Another conversion process commonly applied in ethanol production is simultaneous saccharification and fermentation (SSF). SSF typically leads to higher product yields and requires lower amounts of enzyme because end-product inhibition from cellobiose and glucose formed during enzymatic hydrolysis is reduced (Emert & Katzen, 1980; Emert et al., 1980; Gauss et al., 1976; Spindler et al., 1989; Spindler et al., 1987; Takagi et al., 1977; Wright et al., 1987). Sugar released from cellulose during hydrolysis can be utilized in SSF. Combining SSF with hemicellulose sugar fermentation has attracted attention because of lower costs (Dien et al., 2000; Golias et al., 2002). The SSF process, however, has not been reported for oleaginous organism fermentation.

There are a number of challenges associated with application of the SSF process for lipid production using yeast or fungi: 1) the productivity and energy efficiency of lipid production are relatively low compared to bio-ethanol processes, 2) some toxic compounds that remain after enzymatic hydrolysis of pretreated lignocellulosic biomass may have an inhibitory effect on cell growth, 3) the sugar concentration in the enzymatic hydrolysates is not high enough to support the high cell density culture, 4) there may be a possibility that the cellulases used to hydrolyze the cellulose in the lignocellulosic biomass also have an adverse impact on some microorganisms that contain appreciable amounts of cellulose in their cell walls. SSF is often applied in cellulosic ethanol fermentation to decrease substrate inhibition and integrate the whole process, and the SSF process is also complicated by the fact that the optimum working temperature of most commercial cellulases is significantly higher than that of the microorganisms. Moreover, current SSF technologies designed for bioethanol production are not necessarily directly compatible with microbial lipid production. These strategies need be advanced and carefully integrated with the whole process of lipid accumulation.

Single cell oil (SCO) from microorganisms such as fungi and yeasts (Subramaniam et al., 2010) is considered as a potential feedstock for biofuel production because of advantages in high productivity. Some oleaginous microorganisms can produce lipids in amounts up to 70% of the total dry cell weight (Chen et al., 2009). However, the disadvantage of heterotrophic culture is that it requires an organic carbon source. Thus, many oleaginous yeasts have been studied for lipid accumulation on different substrates, such as industrial glycerol (Meesters et al., 1996; Papanikolaou & Aggelis, 2002), sewage sludge (Angerbauer et al., 2008), whey permeate (Akhtar et al., 1998; Ykema et al., 1988), sugar cane molasses (Alvarez et al., 1992) and rice straw hydrolysate (Huang et al., 2009). The use of non-starch biomass is critical and lignocelluloses with the advantages of its abundance and low cost can be used for organic carbon supply without concern for the "fuel versus food" issue. Since the fatty acid profile of microbial oils is quite similar to that of conventional vegetable oils, oleaginous yeast has been suggested as a favorable microorganism for a sustainable biodiesel industry (Zhao et al., 2010). In addition, previous reports indicated that temperature is an important factor in regulating the fatty acid composition in oleaginous fungi (Kendrick & Ratledge, 1992; Weinstein et al., 2000). Thermophilic fungi have the capability to grow in higher temperature, which is desirable for the SSF process because it would lead to higher cellulase activity.

SUMMARY OF THE INVENTION

In spite of great interest in developing "drop-in" fuels, the availability of feasible technical routes that allow for sustainable production of such fuel in the near-term is limited. The heterotrophic fermentation platform offers various attractive options but suffers from the lack of a sustainable sugar supply, except in cases where lignocellulosic materials are used. In this invention, these challenges were addressed and overcome by taking advantage of the readily available low-cost agricultural biomass/waste for lipid production with oleaginous yeast and fungi using a simultaneous saccharification and fermentation (SSF) process. According to the process, lignocellulosic biomass is first pretreated using any of various known thermochemical pretreatment technologies. Then, liquid and solid fractions of the pretreated biomass are separated. Sugars in the liquid fraction are cultured with oleaginous microorganisms (yeast, fungi) which produce and accumulate lipids. The pretreated solid residues are mixed with oleaginous microorganism inocula and undergo simultaneous saccharification and fermentation (SSF) in the presence of cellulases. The cellulases hydrolyze complex polysaccharides in the solid residues (e.g. cellulose, hemicellulose) and release simple sugars which the microorganisms use for growth and lipid production. Solid and cellulase loadings may be varied as appropriate for particular conditions, e.g. type of microorganism employed, type of biomass, etc. An exemplary oleaginous yeast is *Cryptococcus curvatus* and an exemplary oleaginous fungus is *Mortierella isabellina*, both of which have been successfully used in the process. The results presented in the Examples section demonstrated that the SSF process could be successfully applied to oleaginous fungi and yeasts using cellulosic materials for lipid production, and the co-fermentation of glucose and xylose by *Cryptococcus curvatus* revealed the capability and potential of utilizing pretreated biomass containing both cellulose and hemicelluloses for subsequent SSF processes.

It is an object of this invention to provide methods of producing lipids from lignocellulosic biomass. The methods comprise the steps of i) pretreating said lignocellulosic biomass to form a lignocellulosic feedstock; ii) separating said lignocellulosic feedstock into a solids fraction and a liquid fraction; iii) culturing at least one species of oleaginous yeast or fungus in media comprising said liquid fraction under conditions that allow said oleaginous yeast or fungus to produce and accumulate lipids, and iv) culturing at least one species of oleaginous yeast or fungus in media comprising said solids fraction and one or more cellulase and/or hemicellulase enzymes under conditions which allow said cellulase and/or hemicellulase enzymes to digest cellulose and/or hemicellulose in said solids fraction, and which allow said oleaginous yeast or fungus to employ fermentation to produce and accumulate lipids, and v) extracting said lipids produced in steps iii) and iv) from said oleaginous yeast or fungus. In some embodiments, the media comprising said liquid fraction comprises one or more additional components such as sugars, salts and nitrogen sources, acids and trace elements. In other embodiments, the media comprising said solids fraction comprises one or more additional components selected from the group consisting of sugars, salts and nitrogen sources, acids and trace elements. In yet other embodiments, the pretreatment technologies are selected from dilute acid, hot water, steam explosion, sequential pretreatment by ozone and soaking aqueous ammonia, lime, ammonia soaking and ammonia fiber explosion. In some embodiments of the invention, the liquid fraction contains one of more of xylose, glucose, galactose, and mannose. In other embodiments, the method further comprises the step of processing said liquid fraction to remove at least one of acetic acid, furfural and 5-hydroxymethyl-2-furfural, vanillin, syringaldehyde and p-hydroxybenzaldehyde prior to one or both of said steps of culturing. In some embodiments, the lignocellulosic biomass is selected from wheat straw, barley straw, grass straw, corn stover and sugarcane bagasse, and mixtures thereof. In some embodiments, the oleaginous yeast is selected from the group consisting of *Cryptococcus curvatus, Rhodotorula glutinis, Rhodosporidium toruloides, Lipomyces starkeyi, Yarrowia lipolytica* and *Trichosporon fermentans*. In other embodiments, the oleaginous fungus is selected from the group consisting of *Cunninghamella elegans, Aspergillus terreus, Mortierella vinacea* and *Mortierella isabellina*. In some embodiments, the oleaginous yeast is *Cryptococcus curvatus*. In other embodiments, the oleaginous fungus is *Mortierella isabellina*. In some embodiments of the invention, the method further comprises a step of harvesting said oleaginous yeast or fungus prior to said step of extracting. In other embodiments, the cellulase enzymes are selected from the group consisting of cellulases, β-glucosidases, hemicellulases, β-xylosidases and mixtures thereof. In some embodiments, the method is carried out using a culture process such as batch culture, fed-batch culture, continuous culture, or semi-continuous culture, or mixtures of these, e.g. different stages or steps of the method may employ different culture processes (procedures).

The invention also provides methods of producing biofuel from lignocellulosic biomass. The methods comprise the steps of: i) pretreating said lignocellulosic biomass to form a lignocellulosic feedstock; ii) separating said lignocellulosic feedstock into a solids fraction and a liquid fraction; iii) culturing at least one species of oleaginous yeast or fungus in media comprising said liquid fraction under conditions that allow said oleaginous yeast or fungus to produce and accumulate lipids, and iv) culturing at least one species of oleaginous yeast or fungus in media comprising said solids fraction and one or more cellulase and/or hemicellulase enzymes under conditions which allow said cellulase and/or hemicellulase enzymes to digest cellulose and/or hemicellulose in said solids fraction, and which allow said oleaginous yeast or fungus to employ fermentation to produce and accumulate lipids; v) extracting said lipids produced in steps iii) and iv) from said oleaginous yeast or fungus; and vi) producing biofuel from said lipids. In some embodiments, the media comprising said liquid fraction comprises one or more additional components such as sugars, salts and nitrogen sources, acids and trace elements. In other embodiments, the media comprising said solids fraction comprises one or more additional components selected from the group consisting of sugars, salts and nitrogen sources, acids and trace elements. In yet other embodiments, the pretreatment technologies are selected from dilute acid, hot water, steam explosion, sequential pretreatment by ozone and soaking aqueous ammonia, lime, ammonia soaking and ammonia fiber explosion. In some embodiments of the invention, the liquid fraction contains one of more of xylose, glucose, galactose, and mannose. In other embodiments, the method further comprises the step of processing said liquid fraction to remove at least one of acetic acid, furfural and 5-hydroxymethyl-2-furfural, vanillin, syringaldehyde and p-hydroxybenzaldehyde prior to one or both of said steps of culturing. In some embodiments, the lignocellulosic biomass is selected from wheat straw, barley straw, grass straw, corn stover and sugarcane bagasse, and mixtures thereof. In some embodiments, the oleaginous yeast is selected from the group consisting of *Cryptococcus curvatus, Rhodotorula glutinis, Rhodosporidium toruloides, Lipomyces starkeyi, Yarrowia lipolytica* and *Trichosporon fermentans*. In other embodiments, the oleaginous fungus is selected from the group consisting of *Cunninghamella elegans, Aspergillus terreus, Mortierella vinacea* and *Mortierella isabellina*. In some embodiments, the oleaginous yeast is *Cryptococcus curvatus*. In other embodiments, the oleaginous fungus is *Mortierella isabellina*. In some embodiments of the invention, the method further comprises a step of harvesting said oleaginous yeast or fungus prior to said step of extracting. In other embodiments, the cellulase enzymes are selected from the group consisting of cellulases, β-glucosidases, hemicellulases, β-xylosidases and mixtures thereof. In some embodiments, the method is carried out using a culture process such as batch culture, fed-batch culture, continuous culture, or semi-continuous culture, or mixtures of these, e.g. different stages or steps of the method may employ different culture processes (procedures).

DETAILED DESCRIPTION

Figure 1:
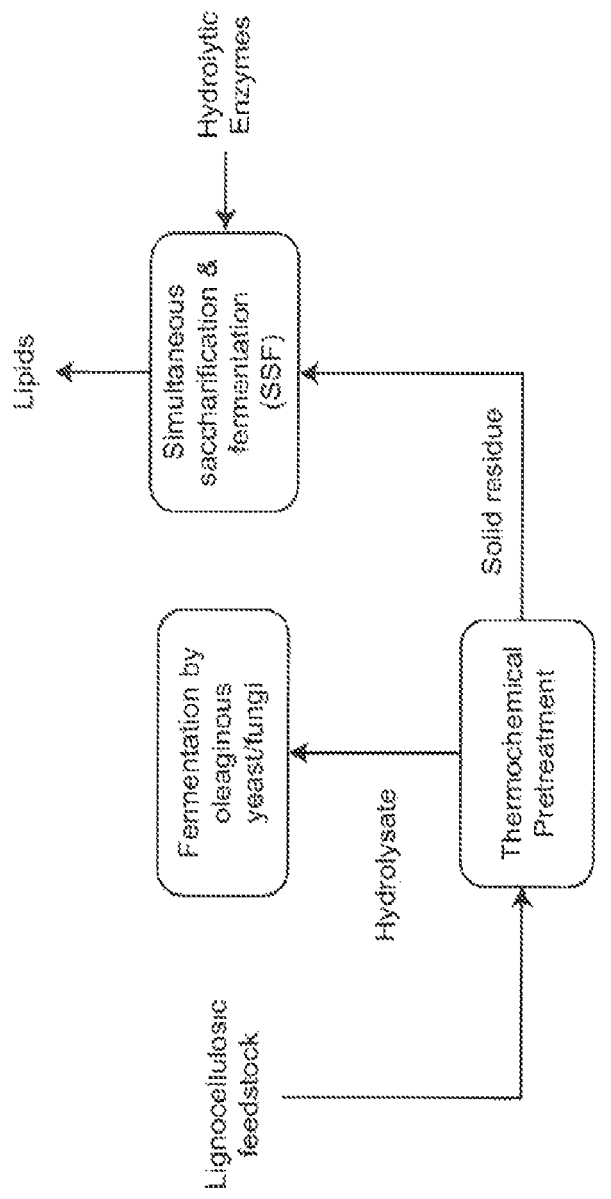
FIG. 1. Schematic representation of biological process converting lignocellulosic feedstock to microbial lipids.
Figure 2A:
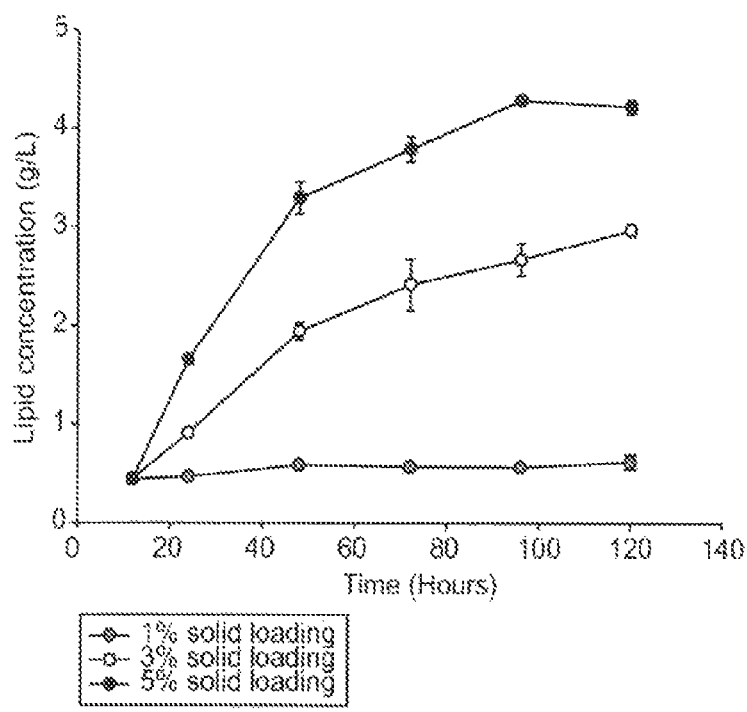
FIG. 2A-D. Lipid concentration in the media cultured by *M. isabellina* at different enzyme loadings (A) 5 FPU/g cellulose, (B) 15 FPU/g cellulose, (C) 30 FPU/g cellulose, (D) 60 FPU/g cellulose FIG. 3A-C. Lipid concentration in the media cultured by *C. curvatus* at different solid loadings (A) 1%, (B) 3%, (C) 5%
Figure 2B:
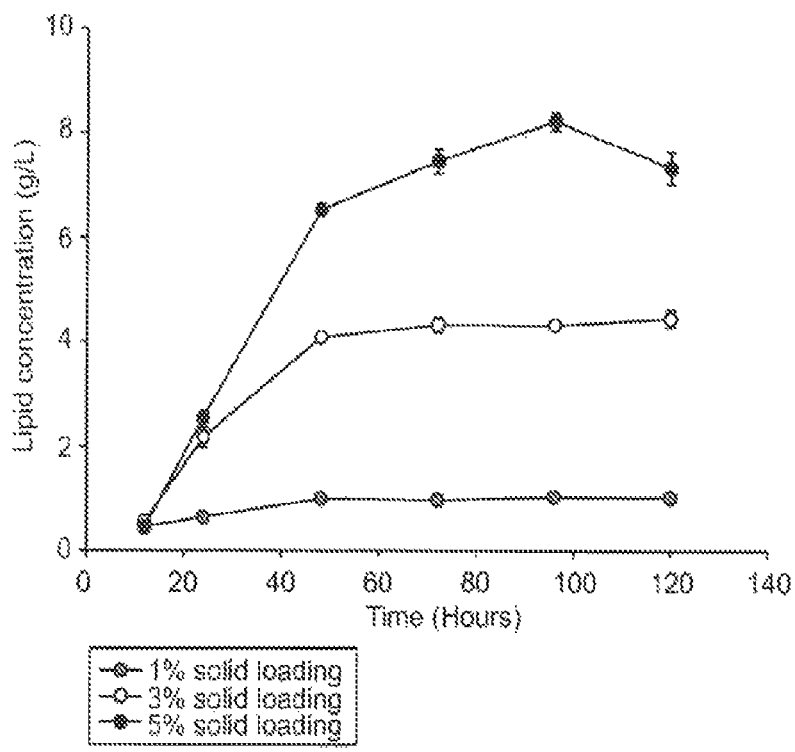
Figure 2C:
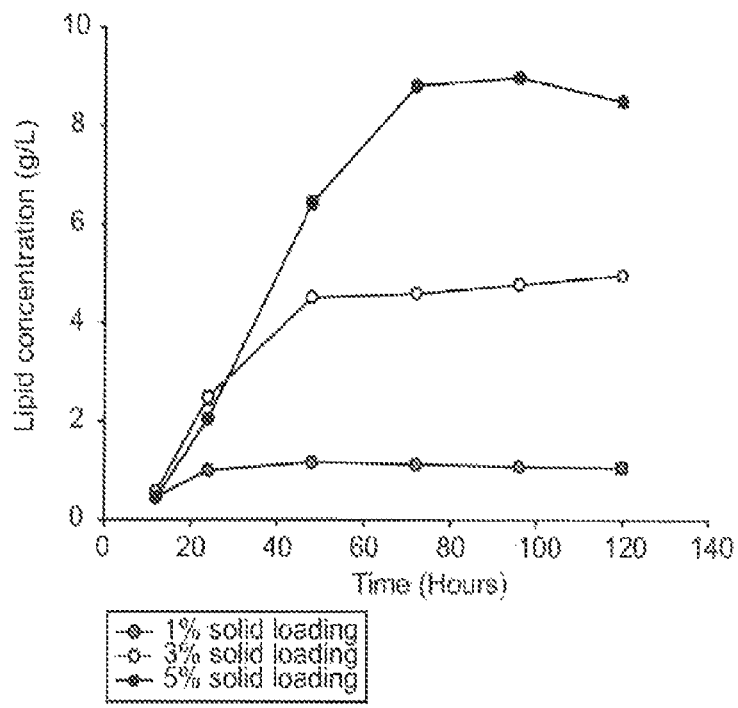
Figure 2D:
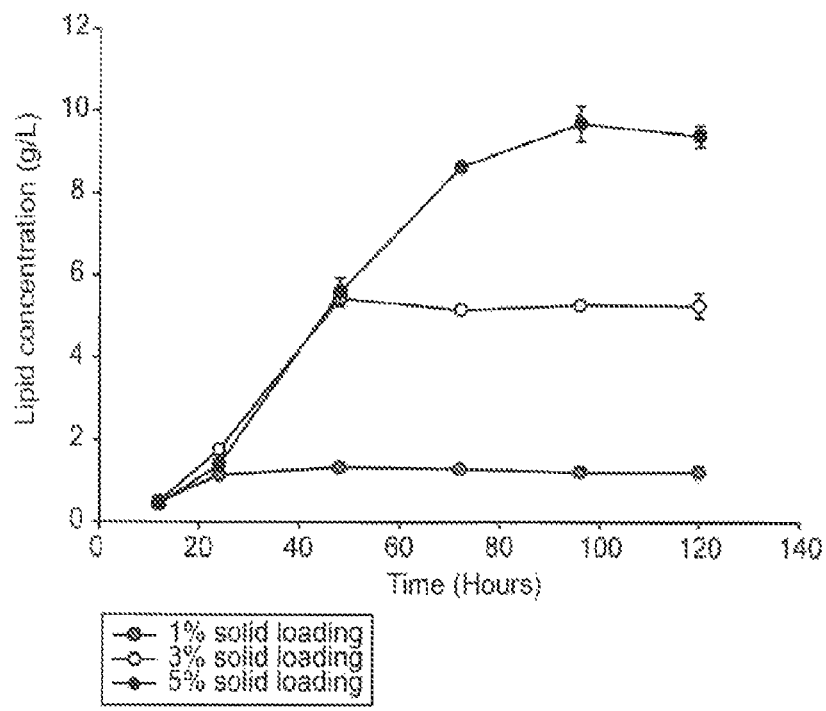

The invention encompasses processes of converting lignocellulosic biomass into lipids which utilize oleaginous yeast and/or fungus. FIG. 1 provides a schematic representation of the method of the invention. The process starts with pretreatment of lignocellulosic biomass, which is required for subsequent simultaneous saccharification and fermentation (SSF). Some chemical/physical pretreatment processes result in hemicellulose depolymerization into mainly xylose and minor amounts of glucose dissolved in the liquid-phase hydrolysate. This liquid fraction of the pretreated hydrolysate containing mixed sugars and their derivatives is used for heterotrophic oleaginous microorganism biomass growth and lipid accumulation. At the same time, oleaginous microorganisms are used in and will adapt to the high cell density SSF process for the conversion of pretreated solid residues during which the cell growth of the microbes (and also lipid production) is supported by the release, by the action of cellulase enzymes, of sugars from cellulose and/or hemicelluloses contained in the solid residues. Once the lignocellulosic sugars are completely utilized, the lipid accumulated in the biomass is extracted and further processed for biofuel production. The method may include a step of separating other products (e.g. by-products) from the lipids.

The following definitions are used throughout:

A "drop-in" fuel is a fuel, usually a biofuel that does not require adaptation of conventional petroleum-based engine fuel systems or fuel distribution networks, prior to use. Drop-in fuel can be used "as is" and/or blended in any amount with other drop-in fuels, drop-in blends, and/or conventional fuels.

By "biomass" we mean biological materials from living or recently living plants, including agricultural waste products. Lignocellulosic biomass typically comprises cellulose and hemicelluloses, and the biomass that is pretreated using dilute acid, hot water/stream, steam explosion, ammonia and lime can be any suitable biomass that contains cellulose and hemicelluloses. Examples of suitable biomass sources include but are not limited to wheat straw, barley straw, rice straw, corn stover, sugarcane, bagasse, switchgrass, etc.

By "cellulases" we mean a suite of enzymes that catalyze celluloses to glucose. Exemplary cellulases are endocellulases, exocellulases and 3-glucosidases. By "hemicellulases" we mean the enzymes that hydrolyze hemicelluloses to pentose (C5 sugars).

Pretreatment

In the practice of the methods of the invention, the lignocellulosic biomass is firstly pretreated to form a lignocellulosic hydrolysate or feedstock. In some embodiments, (TypeA), pretreatment technologies include but are not limited to dilute acid, hot water and steam explosion pretreatment methods. The methods mainly remove pentose from lignocellulosic biomass, such as pentose originally in the hemicellulose part of the biomass. Thus, these pretreatment technologies form a pentose or sugar stream and a solid remainder made of cellulose and lignin. In other embodiments, (Type B), pretreatment technologies include but are not limited to sequential pretreatment by ozone and soaking aqueous ammonia (SAA), lime, ammonia soaking and ammonia fiber explosion pretreatment methods. These methods mainly remove lignin from the lignocellulosic biomass. Thus, these pretreatment technologies generate solid residues containing mostly cellulose and hemicelluloses.

Mechanical disruption of the biomass, e.g. by cutting, shredding, grinding, pulverizing, etc. may also be employed, usually prior to pretreatment.

In one embodiment, the biomass is pretreated by hydrolysis using dilute acid. Suitable dilute acids that may be used include but are not limited to sulfuric acid, nitric acid, hydrochloric acid, and phosphoric acid. Generally, the acid is sulfuric acid. By "dilute" acid we mean acid present at a concentration in the range of from about 0.05% w/v to about 5% w/v, or from about 0.1% w/v to about 2% w/v, and preferably about 1% w/v. The procedure for pretreating the biomass is generally carried out by mixing the biomass with acid under conditions that permit the acid to hydrolyze the hemicellulose components of the biomass, and optionally, the cellulose as well, e.g. at a final pH of from about 1.1 to about 1.5; with the amount of acid ranging from about 0.1 to about 2 weight % based on dry biomass; at a temperature of from about 160° C. to about 220° C.; and for periods of time ranging from about several (e.g. 5-45) seconds to about several (e.g. 1, 2, 3, 4, 5, or more, e.g. 10 or more) minutes (Mosier et al., 2005). Descriptions of dilute acid treatment of biomass may also be found, for example, in: Saeman (1945), Jacobsen and Wyman (2000), and issued U.S. Pat. Nos. 7,993,463 and 5,536,325, the entire contents of each of which are hereby incorporated by reference.

Dilute acid pretreatment of lignocellulosic biomass is known to convert hemicelluloses in biomass to a hydrolysate mainly composed of pentoses, some glucose from cellulases and other degradation products. Conventional dilute acid hydrolysis may be carried out as a one or two-stage process. Two stages may be used to maximize sugar yields from the hemicellulose and cellulose fractions of biomass, with the first stage being operated under milder conditions to hydrolyze hemicellulose, and the second stage being optimized to hydrolyze the more resistant cellulose. According to the present invention, liquid hydrolysate is recovered from after dilute acid treatment (or after both stages in a two-stage process) and is used to culture oleaginous fungi. Advantageously, due to the optimized design of the method, including the selection of optimal fungi, a step of detoxification is not required. Further, due to optimization of culture conditions and selection of optimal fungi, inhibition of microbial fermentation by products formed during pretreatment, which is usually difficult to overcome, is not an issue in the practice of the present invention.

In some embodiments, the procedure for pretreating the biomass is by sequential pretreatment with ozone and soaking aqueous ammonia (SAA) and is generally as follows: biomass is ground to 42-60 mesh size and the moisture content is adjusted to 90% (w/w) with double-distilled water followed by treatment with a stream of ozone-enriched gas (flow rate 2 L/min) at temperature between 0 to 25° C. in a stainless steel reactor for 5 to 30 min. Then the ozone treated biomass is subsequently pretreated with soaking in ammonium hydroxide solution (10 to 30% (w/w) ammonium hydroxide in double-distilled water) with 1:10 to 1:20 (w/v) solid to liquid ratio at 25 to 50° C. for 1 to 6 hours. The obtained biomass is washed twice with water to remove ammonium hydroxide and the pH is adjusted to 5.0 using sulfuric acid for subsequent utilization in simultaneous saccharification and fermentation. Descriptions of ozone pretreatment may also found, for example, in: Cirakovic et al. (2010) and García-Cubero et al. (2009) and for soaking aqueous ammonia can be found, for example in: Kim & Lee (2005), Kim & Lee (2006) and Kim & Lee (2007).

In some embodiments, pretreatment of biomass produces a feedstock or hydrolysate or "pretreated biomass" which comprises a liquid fraction in which sugars and other molecules are dissolved, and a solid fraction containing non-hydrolyzed residue with a high cellulose and/or hemicellulose content. These two fractions can be separated by any of the many methods known to those of skill in the art, e.g. by draining or decanting the liquid, by sedimentation, by centrifugation, by filtration, etc.

Culturing Oleaginous Fungi with Pretreated Biomass Fractions

Depending on which type of pretreatment technology is employed, different culture conversion processes are used for lipid synthesis. For the biomass pretreated by Type A pretreatment technologies, the sugar stream is fermented by oleaginous yeast or fungi. Briefly, the liquid fraction of the pretreated biomass is used as culture medium or as an addition to culture medium for the growth of one or more types of oleaginous yeast or fungi, and sugars dissolved in the liquid fraction are used by the oleaginous microorganisms to accumulate biomass and to synthesize and accumulate lipids. In this embodiment, the remaining solid residues undergo a simultaneous saccharification and fermentation (SSF) process with addition of cellulases. Because of this particular pretreatment, the solid residue contains mostly cellulose which is digested by the cellulases, releasing sugars which are fermented by the oleaginous yeast and/or fungi. In this embodiment, saccharification-fermentation mixture is prepared that includes the solid residues of pretreated biomass, an oleaginous strain, and at least one enzyme that converts polysaccharides of preheated solid residues to fermentable sugars. Additional media components such as sugars, salts and nitrogen sources are typically necessary and included. Components of the preheated solid residues of biomass are saccharified, or hydrolyzed, by one or more of the saccharification enzymes (cellulases and hemicellulases) to release fementable sugars such as glucose and xylose. Sugars are released over time from the preheated biomass. The released sugars are metabolized by the oleaginous strains to produce lipids as a product.

In other embodiments, for biomass preheated by Type B pretreatment technologies, the resulting solid residues are processed using SSF but with the addition of both cellulases and hemicellulases since the residue contains both cellulose and hemicellulose.

Those of skill in the art are familiar with general methods for culturing fungi and yeast, e.g. in liquid culture medium. In some embodiments of the invention, the culture medium contains the liquid fraction from preheated biomass. In this embodiment, the liquid fraction may be treated to remove substances such as inhibitors (e.g. acetic acid, furfural and 5-hydroxymethyl-2-furfural, etc.) or other unwanted (usually non-sugar) substances. In embodiments in which the culture medium contains the solid residue from preheated biomass and may or may not be similarly treated.

In all embodiments, the culture composition may be tailored to suit the particular embodiment, e.g. according to the type of microorganism, the fraction and type of biomass, the type of lipids that are desired, the type of enzymes (if any) that are used, etc. For example, for fungal growth such conditions may include temperatures of from about 25° C. to about 30° C., pH values of from about 5.0 to about 7.0, etc. For yeast growth, such conditions may include temperatures of from about 25° C. to about 30° C., pH values of from about 5.5 to about 8.0, etc. When cellulases and/or hemicelluases are present, the conditions will generally be at a pH value of about 5.0 and a temperature of about 30° C. or higher, in order to allow them to catalyze breakdown of their respective substrates. Additional ingredients may be added to the culture medium prior to or during culture, including but not limited to of sugars, salts, nitrogen sources, acids and trace elements, etc. For cultures using the liquid fraction, the culturing is typically carried out for a period of time ranging from about 36 hours to about 72 hours, and usually for about 48 hours. For cultures using solid residue fractions, SSF is typically carried out for a period of time ranging from about 24 hours to about 96 hours, and usually for about 72 hours. Processes for culturing include but are not limited to batch culture, fed-batch culture, continuous culture, semi-continuous culture process.

SSF is typically carried out using a high density culture. By "high density culture" we mean that the amount of fungal and/or yeast cells in the culture has a density of from about 50 g/L to about 200 g/L, and usually is at least about 100 g/L. Heterotrophic culture is generally carried out at cell densities ranging from about 10 g/L to about 50 g/L.

Additional exemplary fungal culture methods are described, for example, in issued U.S. Pat. No. 7,682,615 to Kristiansen; U.S. Pat. No. 8,211,830 to Bailey; U.S. Pat. No. 8,178,327 to Burk et al.; and U.S. Pat. No. 8,053,217 to Berglund et al, the complete contents of each of which is hereby incorporated by reference.

The invention also encompasses compositions comprising SSF mixtures, e.g. comprising one or more solid residue fractions, plus relevant enzymes (cellulases and/or hemicellulases), plus one or more relevant oleaginous fungus and/or yeast (or a mixture of oleaginous fungi and oleaginous yeast), as described herein.

Oleaginous Fungi and Yeast

Oleaginous yeasts suitable for use in the methods of the invention include but are not limited to: *Cryptococcus curvatus, Rhodotorula glutinis, Rhodosporidium toruloides, Lipomyces starkeyi, Yarrowia lipolytica* and *Trichosporon fermentans*. Suitable oleaginous fungi include but are not limited to *Cunninghamella elegans, Aspergillus terreus, Mortierella vinacea* and *Mortierella isabellina*. The oleaginous yeasts and fungi may be thermophilic and or thermotolerant, i.e. capable of growing (increasing in biomass) and producing and accumulating lipids at elevated temperatures such as at or above about 25, 30, 35, 40, 45, or 50° C. Any type of oleaginous yeast or fungus that is capable of growing in culture as described herein, and which is capable of producing significant quantities of lipids (e.g. at least about 25% dry weight of lipid, or at least about 30, 35, 40, 45, 50, 55, 60, 65 or 70% dry weight of lipid) may be used in the practice of the invention. By "% dry weight" we mean the percentage of lipid per given weight of dry microorganism.

Lipids

Lipids that can be synthesized and accumulated by oleaginous fungi and yeasts using the methods of the invention include but are not limited to those which include one or more of the following fatty acids: myristic, palmitic, palmitoleic, stearic, oleic, linoleic, linolenic, and arachidic acid. Particular lipids include but are not limited to: heptadecenoic acid, behenic acid, lignoceric acid, pentadecanoic acid, hexadecenoic acid, γ-linolenic acid and eicosenoic acid, etc.

The lipids that are generated using the methods of the invention may be used for any suitable purpose. In one embodiment, they are used to produce biofuel, especially a drop-in biofuel. By "biofuel" we mean a fuel made from biologic materials. Exemplary biofuels that may be produced using the lipids generated as described herein include but are not limited to renewable gasoline and diesel, jet fuel and biodiesel. Those of skill in the art are familiar with methods of extracting and processing lipids. After extraction, the oils may be used to form biofuel (e.g. methane, biodiesel, bioethanol and other alcohols, etc.) as described, for example, in issued U.S. Pat. Nos. 7,905,930 and 7,977,076 (Oyler), the complete contents of which are hereby incorporated by reference.

The invention also encompasses lipids and biofuels made by the methods described herein, e.g. a lipid or mixture of lipids made from lignocellulosic biomass which has undergone method steps which include the following:

i) pretreating the lignocellulosic biomass to form a lignocellulosic feedstock;

ii) separating the lignocellulosic feedstock into a solids fraction and a liquid fraction;

iii) culturing at least one species of oleaginous yeast or fungus in media comprising the liquid fraction under conditions that allow the oleaginous yeast or fungus to produce and accumulate lipids, and iv) culturing at least one species of oleaginous yeast or fungus in media comprising the solids fraction and one or more cellulase enzymes under conditions which allow the cellulase enzymes to digest cellulose in said solids fraction, and which allow said oleaginous yeast or fungus to employ fermentation to produce and accumulate lipids, and v) extracting the lipids produced in steps iii) and iv) from said oleaginous yeast or fungus;

as well as biofuels made from such lipids and/or mixtures of lipids.

Figure 5:
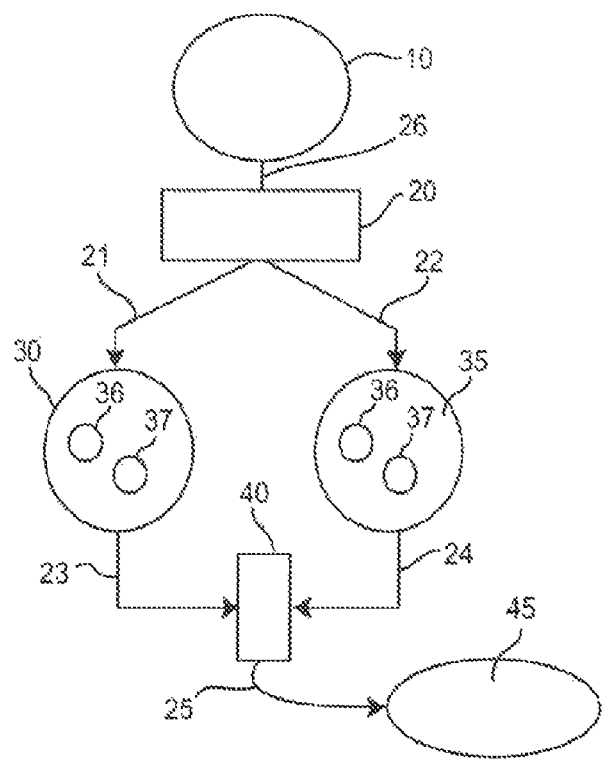
FIG. 5. Schematic illustration of an exemplary system of the invention.

The invention also comprises systems for carrying out the methods described herein. A schematic representation of an exemplary system is shown in FIG. 5, which shows pretreatment container 10, operably connected to separation device 20, which separates a lignocellulosic feedstock produced in pretreatment reactor 10 into liquid and solid fractions. Optional transport or transfer means may be used to transfer the lignocellulosic feedstock to separation device 20, or separation device 20 may be contained within or integrated into pretreatment reactor 10. The liquid fraction is transferred via transport/transfer means 21 (e.g. a pipe) to heterotrophic culture reactor 30, where sugars in the liquid fraction are used by heterotrophic oleaginous yeast and/or fungi to accumulate biomass (increase in cell number and or individual cell size and/or weight) and to produce and accumulate lipids. Suitable culture conditions (e.g. temperature) may be maintained in heterotrophic culture reactor 30 e.g. with thermostat 36, heater 37, etc.) Heterotrophic culture reactor 30 is operably connected (e.g. via optional transport/transfer means 23) to lipid extraction device 40. Meanwhile, the solid fraction is transferred e.g. via transport/transfer means 22 to an SSF culture reactor 35. SSF culture reactor 35 receives and is capable of being regulated (e.g. with a thermostat 36, a heater 37, etc.) so as to foster the culturing of the solid fraction plus suitable oleaginous microorganisms plus suitable enzymes, and to do so at a temperature appropriate for optimized growth of the microorganisms, and lipid production and accumulation by the microorganisms. SSF culture reactor 35 is operably connected (e.g. via an optional transport/transfer means 24) to lipid extraction device 40. Those of skill in the art will recognize that one or more than one lipid extraction device 40 may be present in such a system, and in fact lipid extraction device 40 is optional and/or may not be included in but not directly connected to other system components. Lipids extracted from lipid extraction device 40 are transferred via transport/transfer means 25 (which is optional, and may be a direct means such as a pipe, or indirect such as via containers loaded onto a truck or other mode of transportation). The destination of the lipids is biofuel manufacturing facility 45, which may be directly incorporated into the system (e.g. located as an integral part of the system or located in close proximity such as within 1-5 miles), or located at a distance (e.g. greater than 5 miles).

The following Examples are provide as exemplary illustrations of the practice of the method but should not be construed so as to limit the invention in any way.

All patents, patent applications and published articles cited herein are hereby incorporated by reference in entirety.

All words and terms utilized herein have their ordinary, conventional meaning as used in the art, unless otherwise noted.

EXAMPLES

Example 1

Simultaneous Saccharification and Fermentation of Avicel Cellulose by Oleaginous Fungus for Microbial Oil Production The filamentous fungus *Mortierella isabellina* was selected for single cell oil production by simultaneous saccharification and fermentation (SSF) process. The enzyme mixture of cellulases from Novozyme was prepared in phosphate buffer with pH 5.0 and sterilized by passing through 0.20 μm membrane filters (Millipore, MA). All SSF experiments were conducted in 250 mL flasks with three solid loading levels 1%, 3% and 5% (w/v) and four cellulase loading levels 5, 15, 30, 60 FPU/g cellulose. The cultures were maintained at 28° C. and 180 rpm.

FIG. 2 presents lipid concentrations in the media versus time during SSF with the cellulase loadings at 5 FPU/g (A), 15 FPU/g (B) 30 FPU/g (C), 60 FPU/g (D) respectively. The results clearly supported that cellulose loading was the limitation factor for microbial oil's accumulation in this study. Lipid production constantly accompanied with increasing solid loading from 1% to 5% at all enzyme loading groups (FIG. 2). The highest lipid concentration obtained was 10 g/L at 5% cellulose loading and 60 FPU/g cellulose loading group which reached 20% conversion rate (cellulose-to-lipid) after initial consumption of free sugar in the medium. After 72 hours, the lipid production in all experimental groups was stable. Among the four enzyme loadings, the cellulase loading at 15 FPU/g cellulose was optimal for lipid accumulation by *M. isabellina*.

Example 2

Figure 3A:
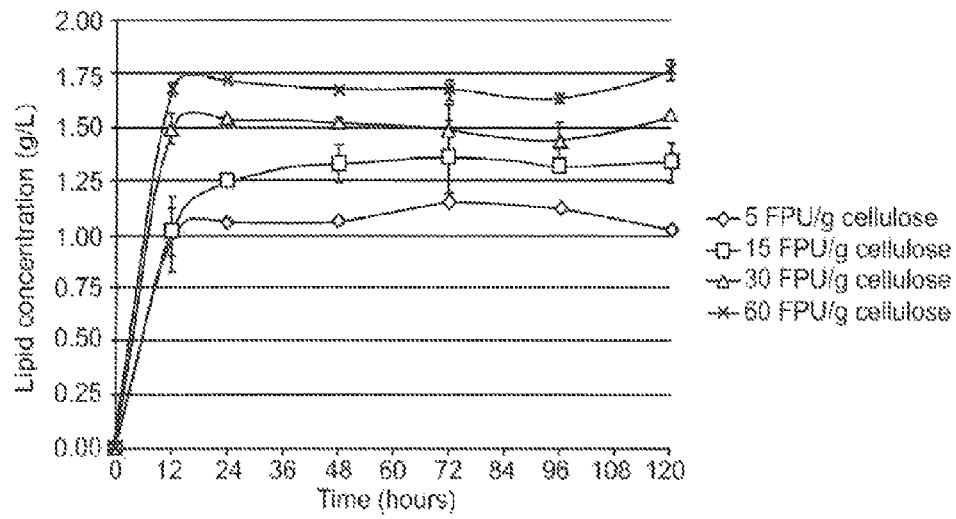
Figure 3B:
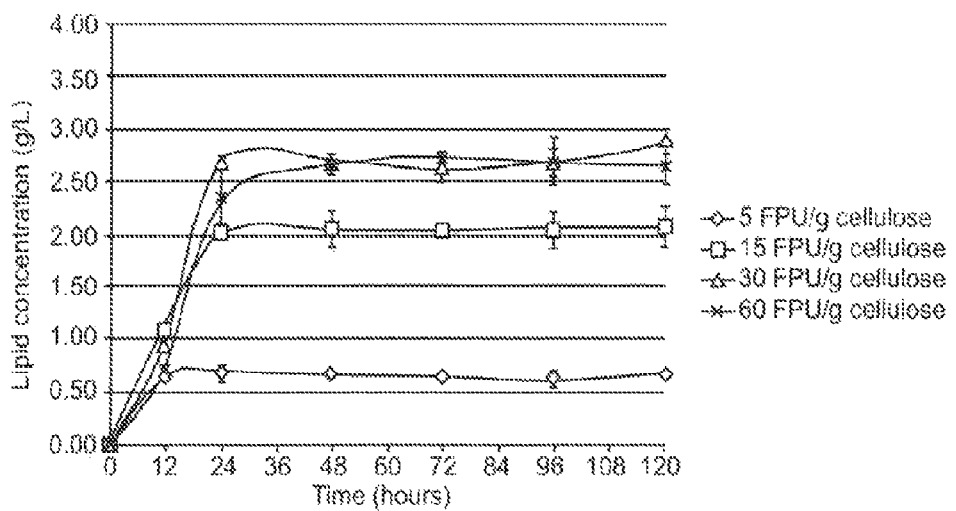
Figure 3C:
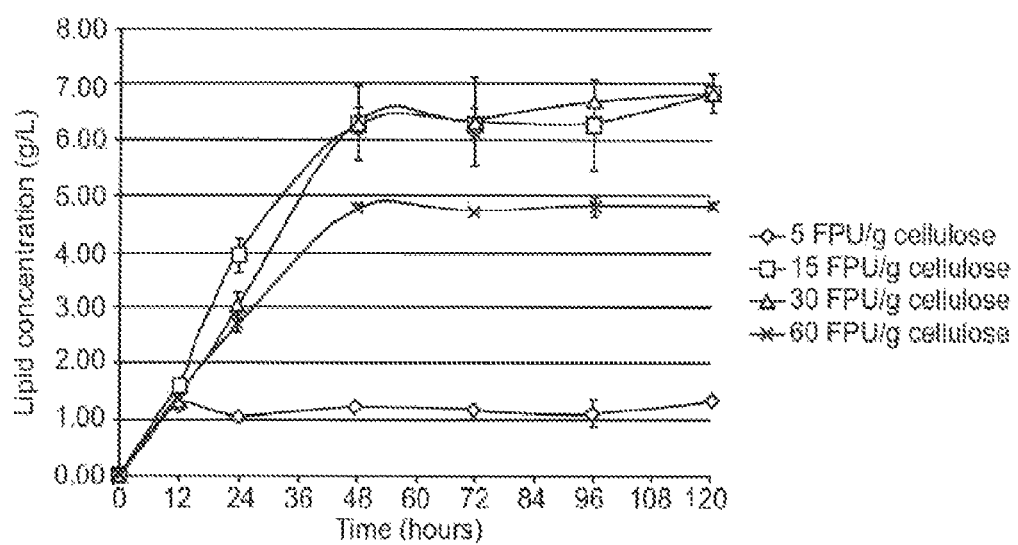
Figure 4A:
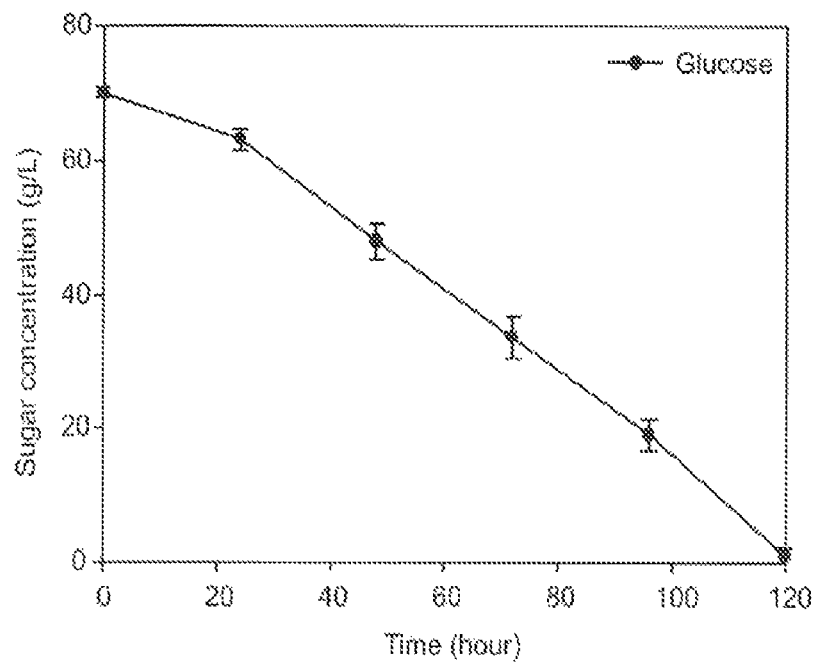
FIG. 4A-G. Sugar consumption by *C. curvatus* cultivated in shake flasks on glucose and xylose mixtures with a total sugar concentration of 70 g/L in different mass ratios (A) glucose as the sole carbon source; (B) glucose:xylose 4:1; (C) glucose:xylose 9:5; (D) glucose:xylose 1:1; (E) glucose:xylose 5:9; (F) glucose:xylose 1:4; (G) xylose as the sole carbon source.
Figure 4B:
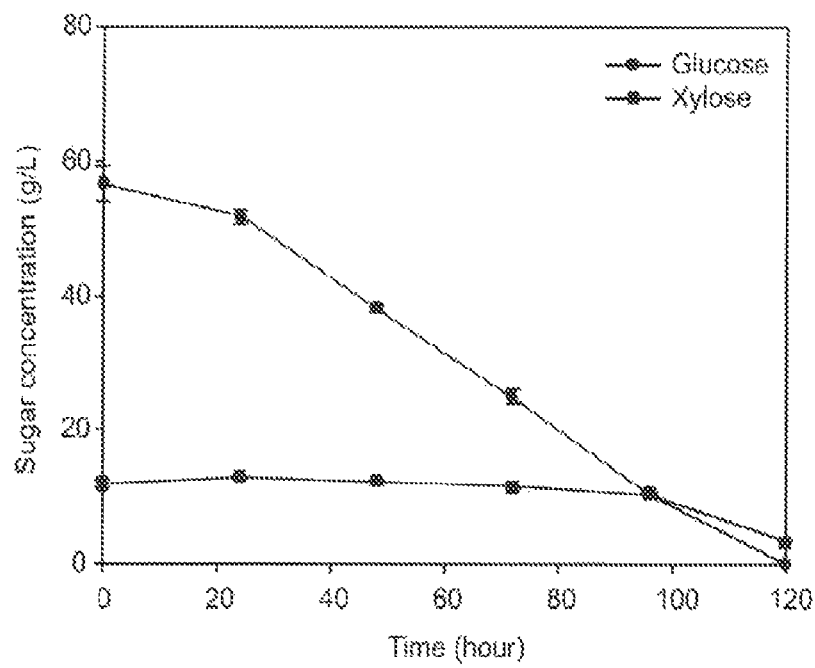
Figure 4C:
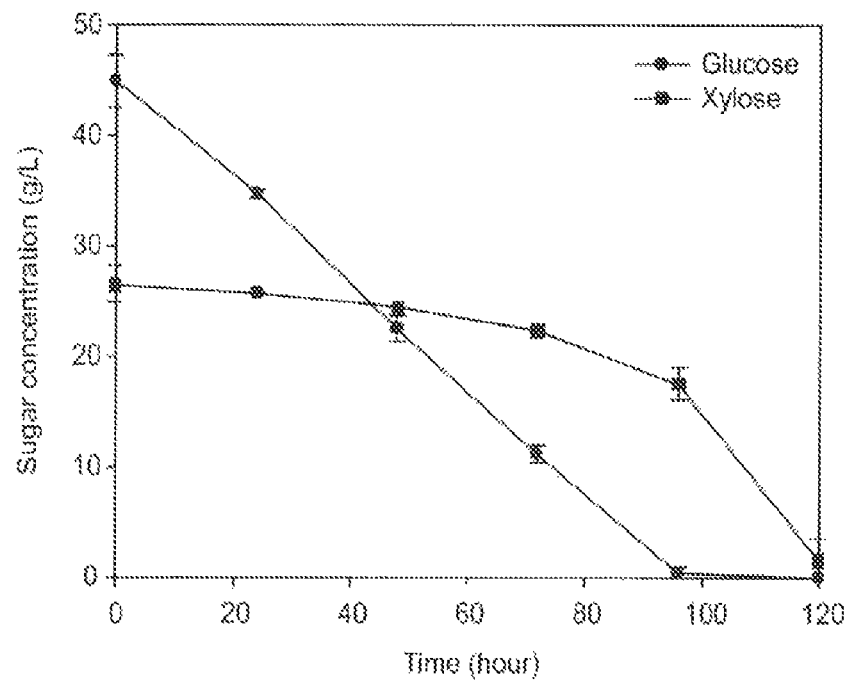
Figure 4D:
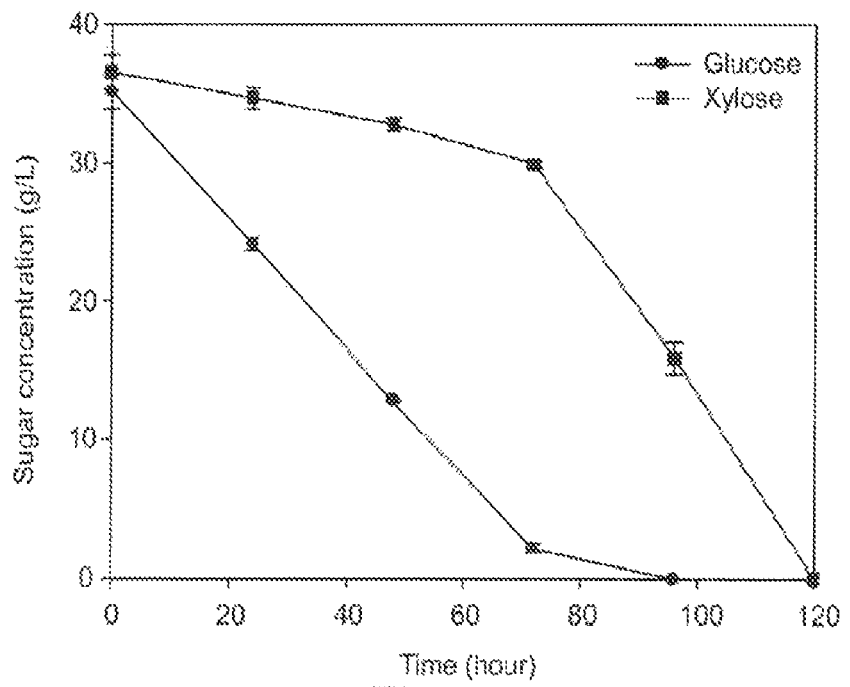
Figure 4E:
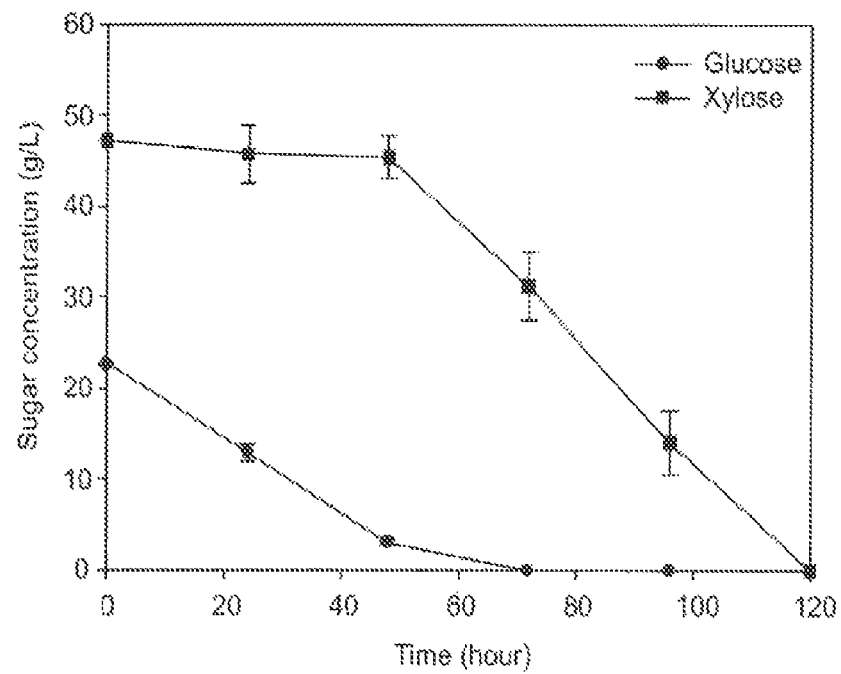
Figure 4F:
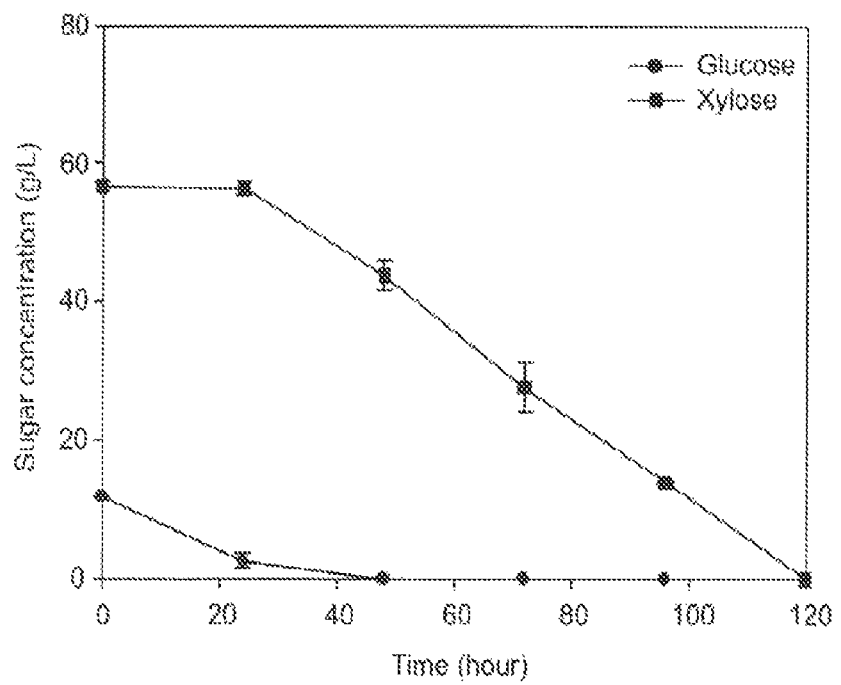
Figure 4G:
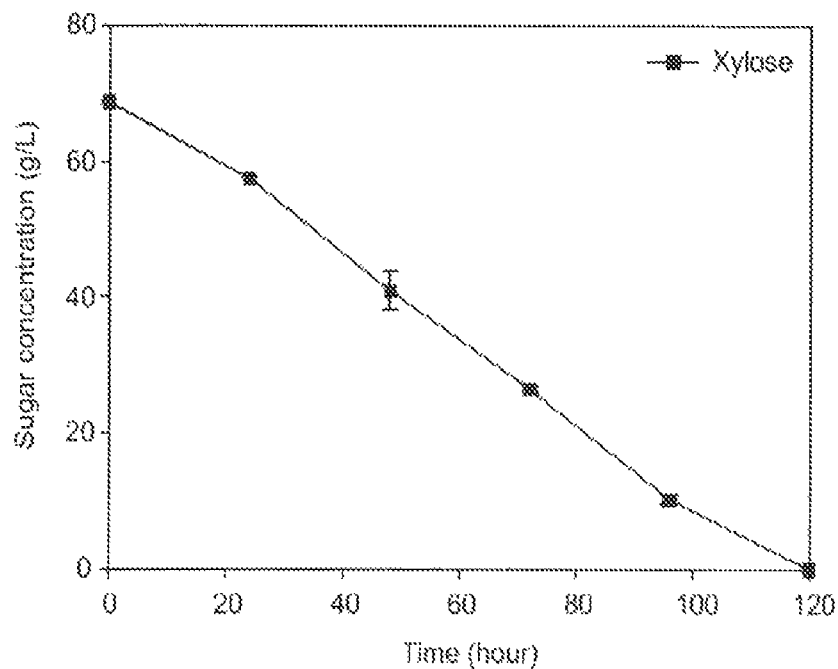

Simultaneous Saccharification and Fermentation of Avicel Cellulose by Oleaginous Yeast for Microbial Oil Production The oleaginous yeast *Cryptococcus curvatus* was applied in SSF process by using Avicel cellulose for microbial oil production. The media preparations and culture conditions were the same as those for the fungus in Example 1. FIG. 3 shows lipid concentrations in the media versus time during SSF with the solid loadings at 1% (A), 3% (B) and 5% (C) respectively. At 1% (w/v) solid loading, the lipid concentrations increased with the cellulase loadings and lipid concentrations reached highest with the cellulase loading at 60 FPU/g cellulose. At 3% (w/v) solid loading, the lipid concentrations were comparable at the cellulase loadings between 30 and 60 FPU/g cellulose. While at 5% (w/v) solid loading, the optimal cellulase loadings in terms of lipid concentrations were 15 and 30 FPU/g cellulose. The results indicated that the solid loadings and cellulase supplement had an interaction effect on the lipid concentration during SSF process by *C. curvatus*. Additionally, the highest cellulose-to-lipid conversion ratio was achieved at 1% (w/v) solid loading and cellulase loading of 60 FPU/g cellulose.

Example 3

Co-Utilization of Glucose and Xylose by *Cryptococcus Curvatus*

During the simultaneous saccharification and fermentation of biomass pretreated by Type B pretreatment technologies, both pentose and hexoses from the biomass will be hydrolyzed and saccharified for lipid production. Therefore, in this work, co-fermentation of glucose and xylose was studied by *C. curvatus* to investigate the potential fermentability of the Type B pretreated biomass during the SSF process.

FIG. 4A-G shows the sugar consumption by *C. curvatus* with different glucose-to-xylose ratios. Generally xylose consumption started once glucose was depleted in the media, while at glucose/xylose ratio of 1:1, xylose was taken up with glucose simultaneously although the uptake rate was much lower than that of glucose. However, among all the culture conditions, the total sugar consumption rates were almost the same. Table 1 presents the biomass, lipid contents and glucose and xylose consumption rates in each culture condition. It was found that xylose is preferred for lipid accumulation and cell growth. Table 2 presents the fatty acid profiles of *C. curvatus* cultured in medium containing glucose and/or xylose as carbon sources at different mass ratios. The results demonstrated that the mixture of glucose and xylose had no significant effects on the fatty acid compositions.

TABLE 1

Results of lipid production by *C. curvatus* cultivated on glucose and xylose mixtures*

| No. | Glucose/Xylose ratio | DCW (g/L) | Lipid content (w/w, %) | DCW yield [a] | Lipid yield [b] | Sugar consumption rate (g/L/h) Glucose | Xylose |
|---|---|---|---|---|---|---|---|
| A | Only glucose | 31.5 | 31.1 | 450 | 140 | 0.583 | — |
| B | 56:14 | 31.1 | 33.9 | 446 | 151 | 0.472 | 0.111 |
| C | 45:25 | 27.3 | 33.8 | 383 | 129 | 0.468 | 0.221 |
| D | 35:35 | 25.8 | 34.7 | 369 | 128 | 0.348 | 0.304 |
| E | 25:45 | 26.5 | 34.5 | 379 | 131 | 0.316 | 0.394 |
| F | 14:56 | 24.7 | 34.4 | 361 | 124 | 0.247 | 0.473 |
| G | Only xylose | 23.8 | 37.7 | 341 | 129 | — | 0.572 |

*All the data were presented as average
[a, b] mg/g sugar consumed

TABLE 2

Fatty acid profiles of *C. curvatus* cultivated on glucose and xylose mixtures*

| No. | Glucose/Xylose ratio | Fatty acid composition | | | | |
|---|---|---|---|---|---|---|
| | | C16:0 | C16:1 | C18:0 | C18:1 | C18:2 |
| A | Only glucose | 32.5 | 1.4 | 15.4 | 42.6 | 6.3 |
| B | 4:1 | 33.8 | 1.6 | 13.9 | 42.5 | 6.6 |
| C | 9:5 | 33.4 | 1.5 | 13.8 | 42.9 | 6.7 |
| D | 1:1 | 32.3 | 1.4 | 14.4 | 43.8 | 6.6 |
| E | 5:9 | 31.6 | 1.3 | 14.6 | 44.7 | 6.6 |
| F | 1:4 | 30.6 | 1.2 | 14.5 | 45.7 | 6.7 |
| G | Only xylose | 31.2 | 1.3 | 15.0 | 45.0 | 6.1 |

*All the data were presented as average

REFERENCES

Akhtar, P., Gray, J. I., Asghar, A. 1998. Synthesis of lipids by certain yeast strains grown on whey permeate. *Journal of Food Lipids*, 5(4), 283-297.

Alvarez, R. M., Rodriguez, B., Romano, J. M., Diaz, A. O., Gomez, E., Miro, D., Navarro, L., Saura, G., Garcia, J. L. 1992. Lipid accumulation in *Rhodotorula glutinis* on sugar cane molasses in single-stage continuous culture. *World Journal of Microbiology & Biotechnology*, 8(2), 214-15.

Angerbauer, C., Siebenhofer, M., Mittelbach, M., Guebitz, G. M. 2008. Conversion of sewage sludge into lipids by *Lipomyces starkeyi* for biodiesel production. *Bioresource Technology*, 99(8), 3051-3056.

Chang, V. S., Burr, B., Holtzapple, M. T. 1997. Lime pretreatment of switchgrass. *Applied Biochemistry Biotechnology*, 63-65, 3-19.

Chang, V. S., Nagwani, M., Holtzapple, M. T. 1998. Lime pretreatment of crop residues bagasse and wheat straw. *Applied Biochemistry Biotechnology*, 74, 135-159.

Chen, X., Li, Z., Zhang, X., Hu, F., Ryu, D. D. Y., Bao, J. 2009. Screening of oleaginous yeast strains tolerant to lignocellulose degradation compounds. *Applied Biochemistry and Biotechnology*, 159(3), 591-604.

Cirakovic, J., Diner, B. A. 2010. OZONE TREATMENT OF BIOMASS TO ENHANCE ENZYMATIC SACCHARIFICATION, E. I. DU PONT DE NEMOURS AND COMPANY.

Dale, R E., Henk, L. L., Shiang, M. 1985. Fermentation of lignocelluosic materials treated by ammonia freeze-explosion. *Developments Industrial Microbiology*, 26(13), 223-233.

Dien, B. S., Nichols, N. N., O'Bryan, P. J., Bothast, R. J. 2000. Development of new ethanologenic *Escherichia coli* strains for fermentation of lignocellulosic biomass. *Applied Biochemistry and Biotechnology*, 84-86, 181-196.

Emert, G. H., Katzen, R. 1980. Gulfs cellulose-to-ethanol process. *Chemtech*, October, 610-614.

Emert, G. H., Katzen, R., Fredrickson, R. E., Kaupisch, K. F. 1980. Gasohol/biomass developments: Economic update of the Gulf cellulose alcohol process. *Chemical Engineering Progress*, September, 47-52.

García-Cubero, M. T., Gonzalez-Benito, G., Indacoechea, I., Coca, M., Bolado, S. 2009. Effect of ozonolysis pretreatment on enzymatic digestibility of wheat and rye straw. *Bioresource Technology*, 100(4), 1608-1613.

Gauss, W. F., Suzuki, S., Takagi, M. 1976. Manufacture of alcohol from cellulosic materials using plural ferments. United States.

Golias, H., Dumsday, G. J., Stanley, G. A., Pamment, N. B. 2002. Evaluation of a recombinant *Klebsiella oxytoca* strain for ethanol production from cellulose by simultaneous saccharification and fermentation: comparison with native cellobiose-utilising yeast strains and performance in co-culture with thermotolerant yeast and *Zymomonas mobilis*. *Journal of Biotechnology*, 96(2), 155-168.

Heitz, M., Capek-Menard, E., Koeberle, P. G., Gagne, J., Chornet, E., Overend, R. P., Taylor, J. D., Yu, E. 1991. Fractionation of *Populus tremuloides* at the pilot plant scale: Optimization of steam pretreatment using Stake II technology. *Bioresource Technology*, 35, 23-32.

Holtzapple, M. T., Jun, J., Ashok, G., Patibandla, S. L., Dale, B. E. 1991. The ammonia freeze explosion (AFEX) process: A practical lignocellulose pretreatment. *Applied Biochemistry Biotechnology*, 28/29, 59-74.

Huang, C., Zang, M.-h., Wu, H., Liu, Q.-p. 2009. Microbial oil production from rice straw hydrolysate by *Trichosporon fermentans*. *Bioresource Technology*, 100(19), 4535-4538.

Iyer, P. V., Wu, Z. W., Kim, S. B., Lee, Y. Y. 1996. Ammonia recycled percolation process for pretreatment of herbaceous biomass. *Applied Biochemistry Biotechnology*, 57-58, 121-132.

Jacobsen S E, Wyman C E. 2000. Cellulose and hemicellulose hydrolysis models for application to current and novel pre-treatment processes. Appl Biochem Biotechnol 84-6: 81-96.

Kendrick, A., Ratledge, C. 1992. Lipid formation in the oleaginous mould *Entomophthora exitalis* grown in continuous culture: effects of growth rate, temperature and dissolved oxygen tension on polyunsaturated fatty acids. *Applied Microbiology and Biotechnology*, 37(1), 18-22.

Kim, T. H., Lee, Y. Y. 2006. Fractionation of corn stover by hot-water and aqueous ammonia treatment. *Bioresource Technology*, 97(2), 224-232.

Kim, T. H., Lee, Y. Y. 2007. Pretreatment of corn stover by soaking in aqueous ammonia at moderate temperatures. *Applied Biochemistry and Biotechnology*, 137-140, 81-92.

Kim, T. H., Lee, Y. Y. 2005. Pretreatment of Corn Stover by Soaking in Aqueous Ammonia Twenty-Sixth Symposium on Biotechnology for Fuels and Chemicals, (Eds.) B. H. Davison, B. R. Evans, M. Finkelstein, J. D. McMillan, Humana Press, pp. 1119-1131.

Mackie, K. L., Brownell, H. H., West, K. L., Saddler, J. N. 1985. Effect of sulfur dioxide and sulphuric acid on steam explosion of aspenwood. *Journal Wood Chemistry Technology*, 5(3), 405-425.

Meesters, P. A. E. P., Huijberts, G. N. M., Eggink, G. 1996. High cell density cultivation of the lipid accumulation yeast *Cryptococcus curvatus* using glycerol as a carbon source. *Applied Microbiology and Biotechnology*, 45(5), 575-579.

Mosier N, Wyman C E, Dale B E, Elander R, Lee Y Y, Holtzapple M Ladisch M (2005). Features of promising technologies for pretreatment of lignocellulosic biomass. Bioresource. Technol., 96(6): 673-686.

Papanikolaou, S., Aggelis, G. 2002. Lipid production by *Yarrowia lipolytica* growing on industrial glycerol in a single-stage continuous culture. *Bioresource Technology*, 82(1), 43-49.

Ramos, L. P., Breuil, C., Saddler, J. N. 1992. Comparison of steam pretreatment of eucalyptus, aspen, and spruce wood chips and their enzymatic hydrolysis. *Applied Biochemistry Biotechnology*, 34135, 37-48.

Saddler, J. N., Ramos, L. P., Breuil, C. 1993. Steam pretreatment of lignocellulosic residues. in: *Bioconversion of Forest and Agricultural Plant Wastes*, (Ed.) J. N. Saddler, C. A. B. International. Wallingford, UK, pp. 73-92.

Saeman J. F. 1945. Kinetics of wood saccharification: Hydrolysis of cellulose and decomposition of sugars at high temperature. *Ind Eng Chem* 37, 43-52.

Spindler, D. D., Wyman, C. E., Grohmann, K. 1989. Evaluation of thermotolerant yeasts in controlled simultaneous saccharifications and fermentations of cellulose to ethanol. *Biotechnology and Bioengineering*, 34(2), 189-195.

Spindler, D. D., Wyman, C. E., Mohagheghi, A., Grohmann, K. 1987. Thermotolerant yeast for simultaneous saccharification and fermentation of cellulose to ethanol. *Applied Biochemistry Biotechnology*, 17, 279-293.

Subramaniam, R., Dufreche, S., Zappi, M., Bajpai, R. 2010. Microbial lipids from renewable resources: production and characterization. *Journal of Industrial Microbiology & Biotechnology*, 37(12), 1271-1287.

Takagi, M., Abe, S., Suzuki, S., Emert, G. H., Yata, N. 1977. A method for production of alcohol directly from cellulose using cellulase and yeast. *Proceedings, Bioconversion Symposium, Delhi, India. Indian Institute of Technology.* pp. 551-571.

Weil, J., Brewer, M., Hendrickson, R., Sarikaya, A., Ladisch, M. R. 1998. Continuous pH monitoring during pretreatment of yellow poplar wood sawdust by pressure cooking in water. *Applied Biochemistry Biotechnology*, 70-72, 91-111.

Weil, J., Sarikaya, A., Rau, S. L., Goetz, J., Ladisch, C. M., Brewer, M., Hendrickson, R., Ladisch, M. R., 1997. Pretreatment of yellow poplar sawdust by pressure cooking in water. *Applied Biochemistry Biotechnology*, 68(1-2), 21-40.

Weinstein, R. N., Montiel, P. O., Johnstone, K. 2000. Influence of growth temperature on lipid and soluble carbohydrate synthesis by fungi isolated from fellfield soil in the maritime Antarctic. *Mycologia*, 92(2), 222-229.

Wright, J. D., Wyman, C. E., Grohmann, K. 1987. Simultaneous Saccharification and Fermentation of Lignocellulose: Process Evaluation. *Applied Biochemistry Biotechnology*, 18, 75-90.

Wyman, C. E., Dale, B. E., Elander, R. T., Holtzapple, M., Ladisch, M. R., Lee, Y. Y. 2005. Coordinated development of leading biomass pretreatment technologies, *Bioresource Technology*, 96(18), 1959-1966.

Yeshitila Asteraye Tsigie, Chun-Yuan Wang, Novy S. Kasim, Quy-Do Diem, Lien-Huong Huynh, Quoc-Phong Ho, Chi-Thanh Truong, Ju, Y.-H. 2012. Oil Production from *Yarrowia lipolytica* Polg Using Rice Bran Hydrolysate. *Journal of Biomedicine and Biotechnology*, 2012.

Ykema, A., Verbree, E. C., Kater, M. M., Smit, H. 1988. Optimization of lipid production in the oleaginous yeast *Apiotrichum curvatura* in whey permeate. *Applied Microbiology and Biotechnology*, 29(2-3), 211-18.

Yoon, H. H., Wu, Z., Lee, Y. Y. 1995. Ammonia recycled percolation process for pretreatment of biomass feedstock. *Applied Biochemistry Biotechnology*, 51-52, 5-20.

Yu, X., Zheng, Y., Dorgan, K. M., Chen, S. 2011. Oil production by oleaginous yeasts using the hydrolysate from pretreatment of wheat straw with dilute sulfuric acid. *Bioresource Technol*, 102(10), 6134-6140.

Zhao, X., Hu, C., Wu, S., Shen, H., Zhao, Z. 2010. Lipid production by *Rhodosporidium tomloides* Y4 using different substrate feeding strategies. *Journal of Industrial Microbiology and Biotechnology*, 1-6.

We claim:

1. A method of producing lipids from lignocellulosic biomass, comprising the steps of:
    i) pretreating said lignocellulosic biomass to form a lignocellulosic feedstock;
    ii) separating said lignocellulosic feedstock into a solids fraction and a liquid fraction;
    iii) culturing at least one species of oleaginous yeast or fungus in culture medium comprising said liquid fraction under conditions that allow said oleaginous yeast or fungus to produce and accumulate lipids,
    iv) culturing *Cryptococcus curvatus* in culture medium comprising said solids fraction and one or more cellulase and/or hemicellulase enzymes under conditions which allow said cellulase and/or hemicellulase enzymes to hydrolyze cellulose and/or hemicellulose in said solids fraction, and which allow said *Cryptococcus curvatus* to employ fermentation to produce and accumulate lipids in an amount of 124 to 151 mg/g, and
    v) extracting said lipids produced in steps iii) and iv) from said lignocellulose biomass.

2. The method of claim 1, wherein said culture medium comprising said liquid fraction comprises one or more additional components selected from the group consisting of sugars, salts and nitrogen sources, acids and trace elements.

3. The method of claim 1, wherein said culture medium comprising said solids fraction comprises one or more additional components selected from the group consisting of sugars, salts and nitrogen sources, acids and trace elements.

4. The method of claim 1, wherein said pretreatment technologies are selected from dilute acid, hot water, steam explosion, sequential pretreatment by ozone and soaking aqueous ammonia, lime, ammonia soaking and ammonia fiber explosion, wherein said dilute acid is present at a concentration of 0.05% w/v to 2% w/v and said hot water is present at a temperature of 160° C. to 190° C.

5. The method of claim 1, wherein said liquid fraction contains one or more of xylose, glucose, galactose, and mannose.

6. The method of claim 1, further comprising the step of processing said liquid fraction to remove at least one of acetic acid, furfural and 5-hydroxymethyl-2-furfural, syringaldehyde and p-hydroxybenzaldehyde prior to one or both of said steps of culturing.

7. The method of claim 1, wherein said lignocellulosic biomass selected from the group consisting of wheat straw, barley straw, grass straw, corn stover, sugarcane bagasse, and mixtures thereof.

8. The method of claim 1, wherein said oleaginous yeast is selected from the group consisting of *Rhodotorula glutinis*, *Rhodosporidium toruloides*, *Lipomyces starkeyi*, *Yarrowia lipolytica* and *Trichosporon fermentans*.

9. The method of claim 1, wherein said oleaginous fungus is selected from the group consisting of *Cunninghamella elegans*, *Aspergillus terreus*, *Mortierella vinacea* and *Mortierella isabellina*.

10. The method of claim 9, wherein said oleaginous fungus is *Mortierella isabellina*.

11. The method of claim 1, further comprising the step of harvesting said oleaginous yeast or fungus prior to said step of extracting.

12. The method of claim 1, wherein said cellulase enzymes hydrolyze cellulose into glucose and said hemicellulase enzymes hydrolyze hemicellulose into corresponding pentoses.

13. The method of claim 1, wherein said method is carried out using a culture process selected from the group consisting of batch culture, fed-batch culture, continuous culture and semi-continuous culture, or a combination of these.

* * * * *